United States Patent
Stegemann et al.

(10) Patent No.: US 9,604,063 B2
(45) Date of Patent: Mar. 28, 2017

(54) METHOD, APPARATUS AND SYSTEM TO IDENTIFY OPTIMAL PACING PARAMETERS USING SENSOR DATA

(75) Inventors: Berthold Stegemann, Aachan (DE); Hans-Juergen Bruns, Eggermühlen (DE)

(73) Assignee: Medtronic, Inc., Minneapolis, MN (US)

( * ) Notice: Subject to any disclaimer, the term of this patent is extended or adjusted under 35 U.S.C. 154(b) by 2377 days.

(21) Appl. No.: 11/554,162

(22) Filed: Oct. 30, 2006

(65) Prior Publication Data
US 2008/0103539 A1 May 1, 2008

(51) Int. Cl.
*A61N 1/362* (2006.01)
*A61N 1/368* (2006.01)

(52) U.S. Cl.
CPC .......... *A61N 1/3627* (2013.01); *A61N 1/3682* (2013.01)

(58) Field of Classification Search
CPC .................... A61N 1/3627; A61N 1/3682
USPC .......................................... 607/9, 17, 18, 25
See application file for complete search history.

(56) References Cited

U.S. PATENT DOCUMENTS

| | | | |
|---|---|---|---|
| 4,873,980 A | 10/1989 | Schaldach | |
| 4,966,146 A | 10/1990 | Webb et al. | |
| 5,292,341 A | 3/1994 | Snell | |
| 5,487,752 A | 1/1996 | Salo et al. | |
| 5,540,727 A | 7/1996 | Tockman et al. | |
| 6,185,459 B1 | 2/2001 | Mehra et al. | |
| 6,832,112 B1* | 12/2004 | Bornzin | 607/9 |
| 2004/0030356 A1 | 2/2004 | Osypka | |
| 2005/0131480 A1 | 6/2005 | Kramer et al. | |
| 2005/0137634 A1* | 6/2005 | Hall et al. | 607/9 |

* cited by examiner

*Primary Examiner* — Michael D Abreu
(74) *Attorney, Agent, or Firm* — Carol F. Barry

(57) ABSTRACT

A method, apparatus, or system to identify optimal parameters for programming a cardiac stimulator by a matrix-based decision algorithm using sensor data representing cardiovascular function. The parameters include pacing intervals optimized concurrently to produce the maximum resulting cardiac function.

22 Claims, 5 Drawing Sheets

METHOD, APPARATUS AND SYSTEM TO IDENTIFY OPTIMAL PACING PARAMETERS USING SENSOR DATA

BACKGROUND

A variety of implantable medical devices (IMDS) provide electrical stimulation to cardiac muscle. Examples of such cardiac stimulators include pacemakers, defibrillators and cardiac resynchronization therapy (CRT) devices. Such devices may improve cardiac rhythm as well as cardiac function. For example, cardiac resynchronization therapy (CRT) has been clinically demonstrated to improve indices of cardiac function in patients suffering from congestive heart failure. CRT involves cardiac pacing that may be applied to one or both ventricles or multiple heart chambers, including one or both atria, to improve cardiac chamber coordination, which in turn is thought to improve pumping efficiency and stroke volume. Follow-up of patients undergoing CRT has shown improvements in clinical indices as well as hemodynamic measures of cardiac function, left ventricular volumes, and wall motion.

The benefits of CRT may derive from the synchronicity that it provides. For example, CRT allows left ventricular synchronicity such that the systolic phase, the diastolic phase and the mitral apparatus activation are coordinated. It also provides for atrio-ventricular synchronicity, resulting in improved diastolic filling and coordinated filling and ejection timing. However, in order to provide synchronicity and the associated benefits, the timing of the electrical stimulation by the CRT device must be appropriate. Therefore the selection of optimal pacing intervals is necessary to maximize these benefits.

Pacing intervals may be preset to a default setting at the time of implantation of the IMD device. Alternatively, selection of pacing intervals may be based on echocardiographic evaluation of cardiac function or a variety of other selection methods that attempt to optimize cardiac function or hemodynamic status. Some IMDs maintain fixed pacing intervals at all times. Others provide various intervals which are selected depending upon heart rate. While such pacing intervals may be adequate, they are not tailored to the individual patient or to the hemodynamic state of the patient at a particular time.

Because patients in need of cardiac stimulating IMDs are heterogeneous, the same pacing intervals may not be optimal for all patients. For example, some patients have ischemic heart disease while others do not. In addition, various cardiac factors may change throughout the day depending on the amount of activity of the patient and other factors. Thus the degree of ischemia, electrical activation, mechanical activation, loading conditions and degree of mitral insufficiency are different from patient to patient. In addition, these characteristics vary for individual patients throughout the day. Because of this variability, it is desirable for the pacing intervals to be optimized for each individual as well and to vary depending upon the hemodynamic state of that individual in order to optimize cardiac function.

DETAILED DESCRIPTION

Figure 1:
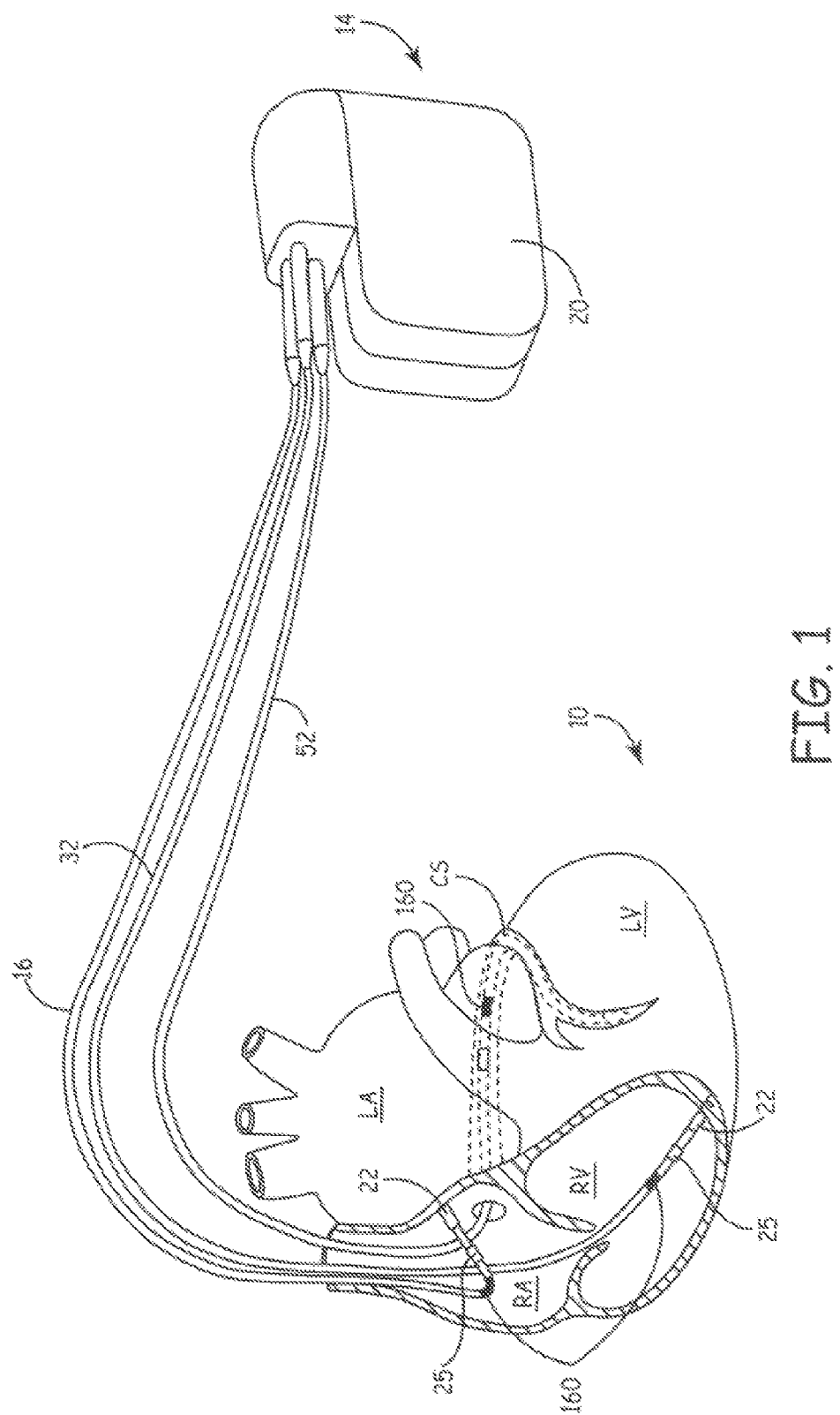
FIG. 1 is a schematic diagram depicting a multi-channel, atrial and biventricular, monitoring/pacing implantable medical device (IMD) in which embodiments of the invention may be implemented.

The following detailed description should be read with reference to the drawings, in which like elements in different drawings are numbered identically. The drawings depict selected embodiments and are not intended to limit the scope of the invention. It will be understood that embodiments shown in the drawings and described below are merely for illustrative purposes, and are not intended to limit the scope of the invention as defined in the claims.

Optimal pacing intervals provide for improved cardiac function in a variety of ways. For example, an optimal AV delay may improve cardiac function by allowing complete filling of the ventricles, by causing the ventricular contraction to occur when ventricular filling is complete, or by causing optimal left ventricular coordination. Similarly, an optimal VV interval may improve cardiac function by providing for a more coordinated left ventricular mechanical activity and electrical activation and can help to compensate for some left ventricular heterogeneity and variability in conduction velocity. Optimization of pacing parameters can increase the likelihood that a patient will have a beneficial response to the device and can result in a greater increase in cardiac function.

Implantable medical devices (IMDs) useful for this invention include devices which provide cardiac resynchronization therapy and cardiac potentiation therapy as well as other cardiac stimulation devices. FIG. 1 is a schematic representation of an implantable medical device (IMD) 14 that may be used in accordance with certain embodiments of the invention. The IMD 14 may be any device that is capable of measuring hemodynamic parameters (e.g., blood pressure signals) from within a patient's cardiovascular system such as within a ventricle of a patient's heart, and which may further be capable of measuring other signals, such as the patient's electrogram (EGM and/or ECG).

In FIG. 1, heart 10 includes the right atrium (RA), left atrium (LA), right ventricle (RV), left ventricle (LV), and the coronary sinus (CS) extending from the opening in the right atrium laterally around the atria to form the great vein.

FIG. 1 depicts IMD 14 in relation to heart 10. In certain embodiments, IMD 14 may be an implantable, multi-channel cardiac pacemaker that may be used for restoring AV synchronous contractions of the atrial and ventricular chambers and simultaneous or sequential pacing of the right and left ventricles. The timing of the contraction may be controlled by the pacing parameters or pacing intervals of the IMD, including, for example, the atrial-ventricular (AV) delay and the interventricular (VV) delay. Embodiments of the invention optimize pacing intervals by selecting pacing intervals which produce the maximum cardiac function.

Three endocardial leads 16, 32 and 52 connect the IMD 14 with the RA, the RV and the LV, respectively. Each lead has at least one electrical conductor and pace/sense electrode, and a can electrode 20 may be formed as part of the outer surface of the housing of the IMD 14. The pace/sense electrodes and can electrode 20 may be selectively employed to provide a number of unipolar and bipolar pace/sense electrode combinations for pacing and sensing functions. The depicted positions in or about the right and left heart chambers are merely exemplary. Moreover other leads and pace/sense electrodes may be used instead of the depicted leads and pace/sense electrodes.

It should be noted that the IMD 14 may also be an implantable cardioverter defibrillator (ICD), a cardiac resynchronization therapy (CRT) device, an implantable hemodynamic monitor (IHM), or any other such device or combination of devices, according to various embodiments of the invention.

Typically, in pacing systems of the type illustrated in FIG. 1, the electrodes designated above as "pace/sense" electrodes are used for both pacing and sensing functions. In accordance with one aspect of the present invention, these "pace/sense" electrodes can be selected to be used exclusively as pace or sense electrodes or to be used in common as pace/sense electrodes in programmed combinations for sensing cardiac signals and delivering pace pulses along pacing and sensing vectors.

In addition, some or all of the leads shown in FIG. 1 could carry one or more sensors, such as pressure sensors for measuring systolic and diastolic pressures. Alternatively or additionally, the leads may carry other sensors such as impedence sensors. Impedance sensors may be spaced in a series for deriving volumetric measurements of the expansion and contraction of the RA, LA, RV and LV or providing a measure of thoracic fluid accumulation and thus cardiac congestion. Other sensors which may be included in one or more leads include accelerometers, pressure sensors, oxymeters, flow sensors, and impendence sensors, for example. Sensors may be used to measure cardiac function during optimization of pacing parameters.

The leads and circuitry described above can be employed to record EGM and/or ECG signals, blood pressure signals, impedance values over certain time intervals and other sensor data. The recorded data may be periodically telemetered out to a programmer operated by a physician or other healthcare worker in an uplink telemetry transmission during a telemetry session, for example.

Figure 2:
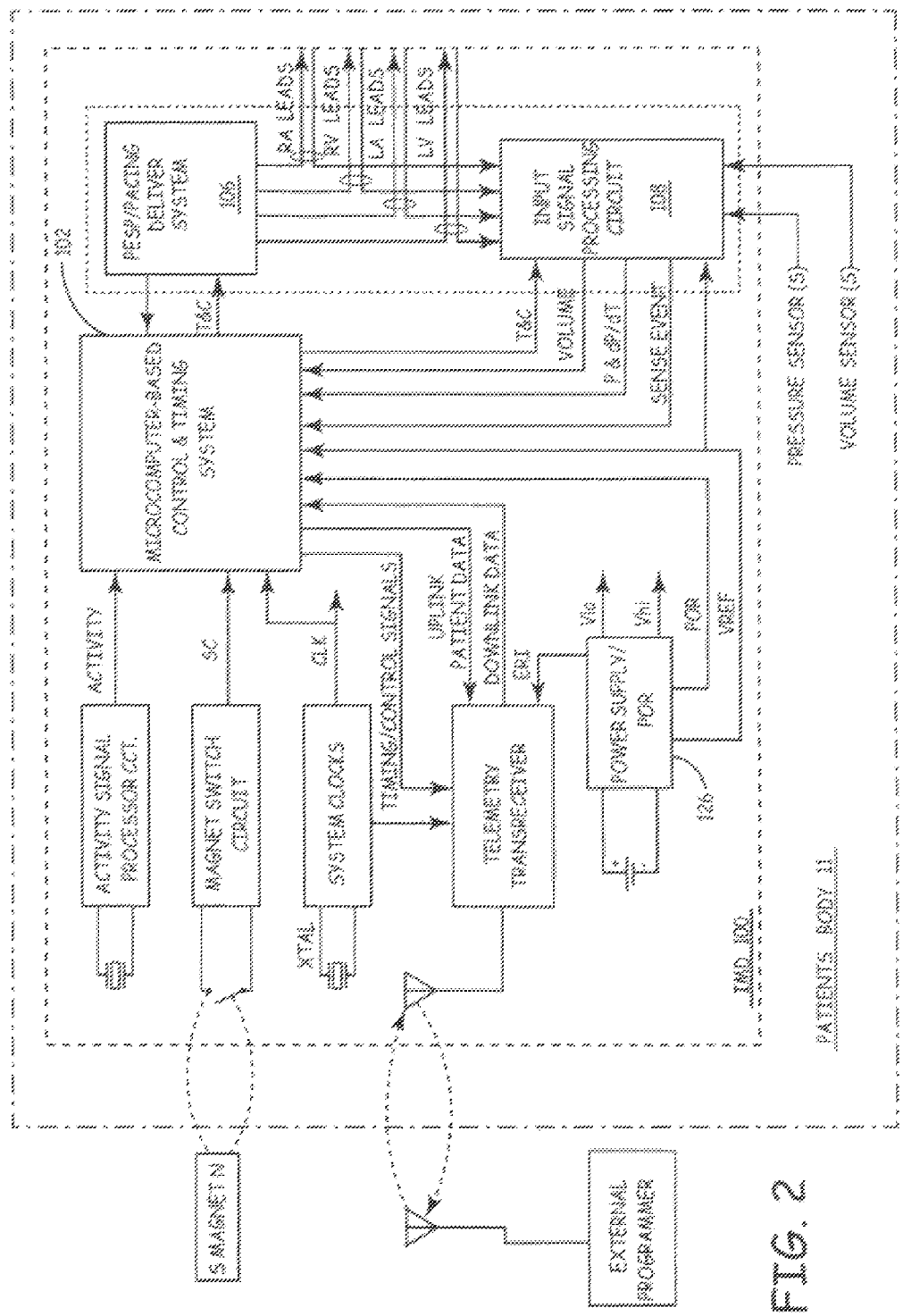
FIG. 2 is a simplified block diagram of an embodiment of IMD circuitry and associated leads that may be employed in the system of FIG. 1 to enable selective therapy delivery and monitoring in one or more heart chamber.

FIG. 2 depicts a system architecture of an exemplary multi-chamber monitor/sensor 100 implanted into a patient's body 11 that provides delivery of a therapy and/or physiologic input signal processing. The typical multi-chamber monitor/sensor 100 has a system architecture that is constructed about a microcomputer-based control and timing system 102 which varies in sophistication and complexity depending upon the type and functional features incorporated therein. The functions of microcomputer-based multi-chamber monitor/sensor control and timing system 102 are controlled by firmware and programmed software algorithms stored in RAM and ROM including PROM and EEPROM and are carried out using a CPU or ALU of a typical microprocessor core architecture.

The therapy delivery system 106 can be configured to include circuitry for delivering cardioversion/defibrillation shocks and/or cardiac pacing pulses delivered to the heart or cardiomyostimulation to a skeletal muscle wrapped about the heart. Alternately, the therapy delivery system 106 can be configured as a drug pump for delivering drugs into the heart or other body areas to alleviate heart failure or to operate an implantable heart assist device or pump implanted in patients awaiting a heart transplant operation.

The input signal processing circuit 108 includes at least one physiologic sensor signal processing channel for sensing and processing a sensor derived signal from a physiologic sensor located in relation to a heart chamber or elsewhere in the body. Examples illustrated in FIG. 2 include pressure and volume sensors, but could include other physiologic or hemodynamic sensors, such as $pO_2$, temperature, pH, blood flow, filling pressure and metabolite levels.

Figure 3:
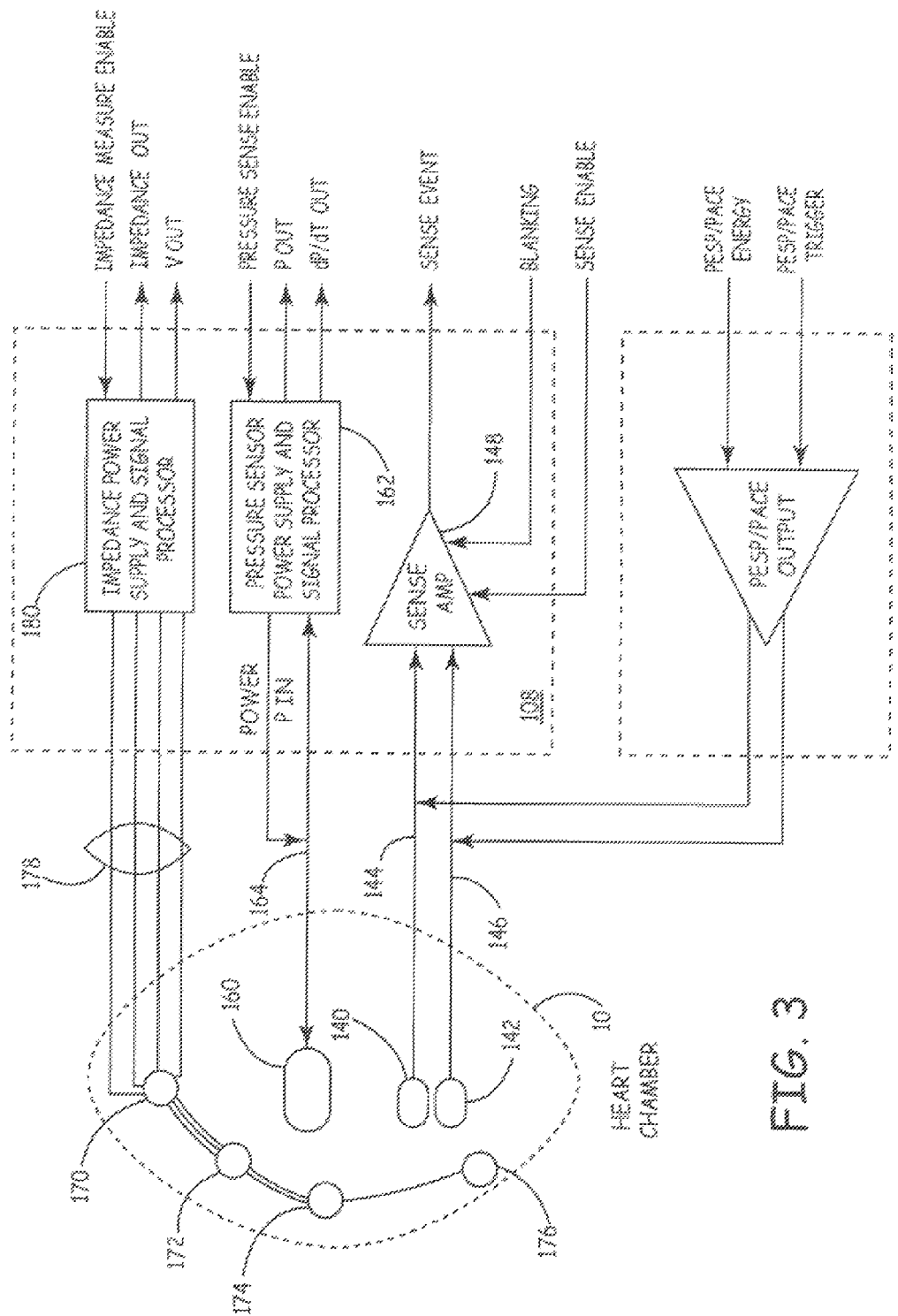
FIG. 3 is a simplified block diagram of a single monitoring and pacing channel for acquiring pressure, impedance and cardiac EGM signals employed in monitoring cardiac function and/or delivering therapy, including pacing therapy, in accordance with embodiments of the invention.

FIG. 3 schematically illustrates one pacing, sensing and parameter measuring channel in relation to one heart chamber. A pair of pace/sense electrodes 140, 142, a pressure sensor 160, and a plurality, e.g., four, impedance measuring electrodes 170, 172, 174, 176 are located in operative relation to the heart 10.

The pair of pace/sense electrodes 140, 142 are located in operative relation to the heart 10 and coupled through lead conductors 144 and 146, respectively, to the inputs of a sense amplifier 148 located within the input signal processing circuit 108. The sense amplifier 148 is selectively enabled by the presence of a sense enable signal that is provided by control and timing system 102. The sense amplifier 148 is enabled during prescribed times when pacing is either enabled or not enabled in a manner known in the pacing art. The blanking signal is provided by control and timing system 102 upon delivery of a pacing or PESP pulse or pulse train to disconnect the sense amplifier inputs from the lead conductors 144 and 146 for a short blanking period in a manner well known in the art. The sense amplifier provides a sense event signal signifying the contraction of the heart chamber commencing a heart cycle based upon characteristics of the EGM and/or ECG. The control and timing system responds to non-refractory sense events by restarting an escape interval (EI) timer timing out the EI for the heart chamber, in a manner well known in the pacing art.

The pressure sensor 160 is coupled to a pressure sensor power supply and signal processor 162 within the input signal processing circuit 108 through a set of lead conductors 164. Lead conductors 164 convey power to the pressure sensor 160, and convey sampled blood pressure signals from the pressure sensor 160 to the pressure sensor power supply and signal processor 162. The pressure sensor power supply and signal processor 162 samples the blood pressure impinging upon a transducer surface of the sensor 160 located within the heart chamber when enabled by a pressure sense enable signal from the control and timing system 102. Absolute pressure (P), developed pressure (DP) and pressure rate of change (dP/dt) sample values can be developed by the pressure sensor power supply and signal processor 162 or by the control and timing system 102 for storage and processing.

A variety of hemodynamic parameters may be recorded including, for example, right ventricular (RV) systolic and diastolic pressures (RVSP and RVDP), left ventricular (LV) systolic and diastolic pressures (LVSP and LVDP), estimated pulmonary artery diastolic pressure (ePAD), pressure changes with respect to time (dP/dt), mechanical pre-ejection interval (mPEI), duration of mechanical systole (MSYS), duration of mechanical diastole (mDIA), heart rate, activity, and temperature. Some parameters may be derived from others, rather than being directly measured. For example, the ePAD parameter may be derived from RV pressures at the moment of pulmonary valve opening, and heart rate may be derived from information in an intracardiac electrogram (EGM) recording.

The set of impedance electrodes 170, 172, 174 and 176 is coupled by a set of conductors 178 and is formed as a lead that is coupled to the impedance power supply and signal processor 180. Impedance-based measurements of cardiac parameters such as stroke volume are known in the art, such as an impedance lead having plural pairs of spaced surface electrodes located within the heart 10. The spaced apart electrodes can also be disposed along impedance leads lodged in cardiac vessels, e.g., the coronary sinus and great vein or attached to the epicardium around the heart chamber. The impedance lead may be combined with the pace/sense and/or pressure sensor bearing lead.

The data stored by IMD 14 may include continuous monitoring of various parameters, for example recording intracardiac EGM data at sampling rates as fast as 256 Hz or faster. In certain embodiments of the invention, an IHM may alternately store summary forms of data that may allow storage of data representing longer periods of time and/or different physiological conditions such as exercise. In one embodiment, hemodynamic pressure parameters may be summarized by storing a number of representative values that describe the hemodynamic parameter over a given storage interval. The mean, median, an upper percentile, and a lower percentile are examples of representative values that may be stored by an IHM to summarize data over an interval of time (e.g., the storage interval). In one embodiment of the invention, a storage interval may contain six minutes of data in a data buffer, which may be summarized by storing a median value, a 94th percentile value (i.e., the upper percentile), and a 6th percentile value (i.e., the lower percentile) for each hemodynamic pressure parameter being monitored. In this manner, the memory of the IHM may be able to provide weekly or monthly (or longer) views of the data stored. The data buffer, for example, may acquire data sampled at a 256 Hz sampling rate over a 6 minute storage interval, and the data buffer may be cleared out after the median, upper percentile, and lower percentile values during that 6 minute period are stored. It should be noted that certain parameters measured by the IHM may be summarized by storing fewer values, for example storing only a mean or median value of such parameters as heart rate, activity level, and temperature, according to certain embodiments of the invention.

Hemodynamic parameters that may be monitored in accordance with various embodiments of the invention include parameters that are directly measured, such as RVDP and RVSP, as well as parameters that may be derived from other pressure parameters, such as estimated pulmonary artery diastolic pressure (ePAD), rate of pressure change (dP/dt), etc.

Certain embodiments of the present invention optimize pacing intervals by varying the intervals and observing the resultant cardiac function. A computer readable medium may be included in the device and programmed to perform the optimization. Appropriate pacing intervals which may be optimized according to embodiments of this invention include the AV interval, including right atrium to right ventricle as well as right atrium to left ventricle interval, the VV interval, and the pre-excitation interval (PEI).

Atrial activation may be intrinsic or may be stimulated by the IMD during optimization. The device could provide single, dual, triple or quadruple chamber stimulation. Alternatively, it could provide stimulation outside of the heart such as by an epicardial patch or other device, or through a combination of endocardial and extra-cardiac stimulation.

Cardiac function may be assessed using a sensor which is part of the IMD and which measures a variable related to cardiac function. For example, an IMD such as a cardiac resynchronization device providing three chamber pacing and having a sensor for measuring right ventricular (RV) pressure is appropriate for some embodiments. In other embodiments, a left ventricular (LV) pressure sensor is appropriate, or both an RV and an LV pressure sensor. Measures of cardiac function which may be detected using the sensor include cardiac output, cardiac flow, arterial pressure, myocardial acceleration, impedance, flow, ejection fraction, degree of mitral regurgitation and tensiometric measurements. Other pressure related measurements include maximum, minimum and average pressure in the right atrium, right ventricle, left atrium or left ventricle, dP/dt (change in pressure over time), $dP/dt_{max}$, $dP/dt_{min}$, end systolic pressure, end diastolic pressure and pulse pressure. Alternatively, peripheral measurements including variables such as pulse pressure or oxygenation level may be evaluated as measures of cardiac function. Although measures of cardiac function such as RV pressure and LV pressure may vary throughout the cycle of the heart beat, a measurement such as the peak or the average during a single cycle, may be selected to represent the value of the cardiac function measurement for a particular beat.

One method of pacing interval optimization is sequential optimization of the intervals. Sequential optimization entails optimizing a single pacing interval while other pacing intervals are held constant. The optimal value of the first pacing interval is identified by cycling the pacing interval through a set of values and measuring cardiac function at each pacing interval. The interval which results in the greatest cardiac function is selected as optimal and is applied by the IMD. A second pacing interval is then optimized in the same manner, while the first interval is held at the previously identified optimal value. For example, the AV interval may be varied through a set of values, while the VV is held at a default or previously determined value. The optimal AV value would be the interval that produces the maximum measure of cardiac function, such as maximum LV and/or RV dP/dt, as detected by an IMD sensor. After the optimal AV interval is determined, the device would then reset the AV interval to the optimum AV interval and would proceed to optimize the VV interval by cycling through a set of VV values to identify the VV interval which produces the maximum cardiac function. Thus the optimal pacing interval is determined for each interval separately, in a sequential manner. However, because the pacing intervals interact to effect cardiac function, such sequential optimization regimens may not identify the combination of pacing intervals which results in the best cardiac function.

Figure 4:
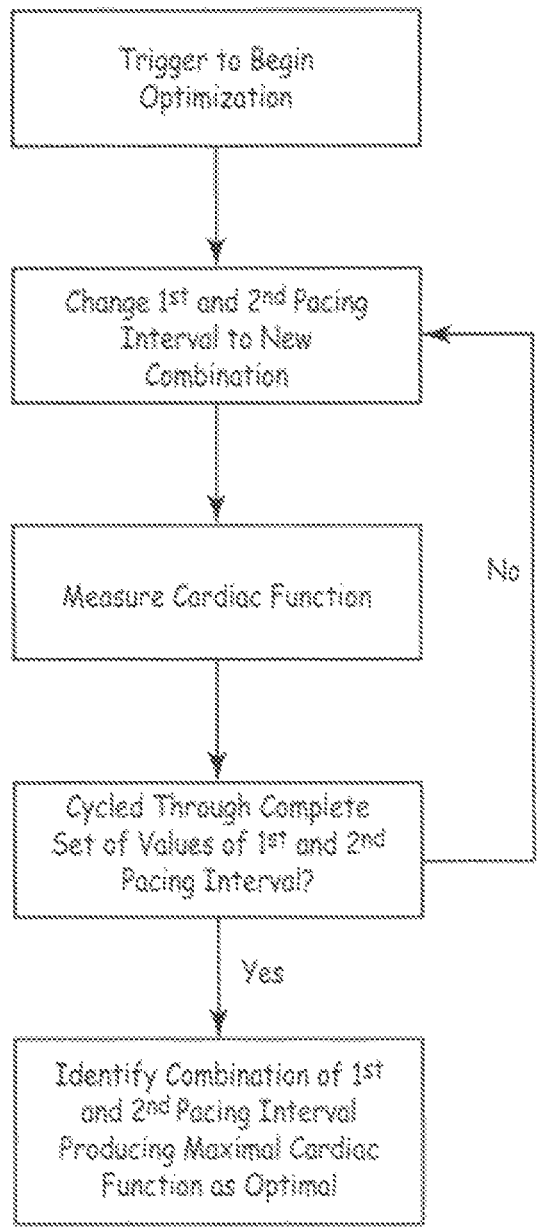
FIG. 4 is a flow chart demonstrating a method of concurrently optimizing two pacing intervals.

Embodiments of this invention optimize two or more pacing intervals concurrently. An example of a method of concurrently optimizing two pacing intervals is demonstrated in FIG. 4. As shown in FIG. 4, optimization begins when the IMD is triggered to start the process 400. A first pacing interval and a second pacing interval are set to a new combination of values 402 and cardiac function is measured 404. The first and second pacing interval are simultaneously iterated through a set of values and cardiac function is measured at each combination until they have cycled through a complete set of values 406. The combination of first pacing interval and second pacing interval which produces the maximum cardiac function, as measured by the IMD sensor, is the optimal combination of optimal pacing intervals 408.

In some embodiments, the AV and the VV interval are concurrently optimized. In such embodiments, AV and VV are simultaneously varied through a set of possible values. At each combination of AV and WV, a measure of cardiac function such as LV and/or RV dP/dt max is obtained. The combination of AV and VV which produces the maximum cardiac function may be determined to be the optimal combination of intervals. In this way, the optimization of the two intervals is performed concurrently, providing a more refined result which may vary from the optimal intervals identified by sequential optimization.

Figure 5:
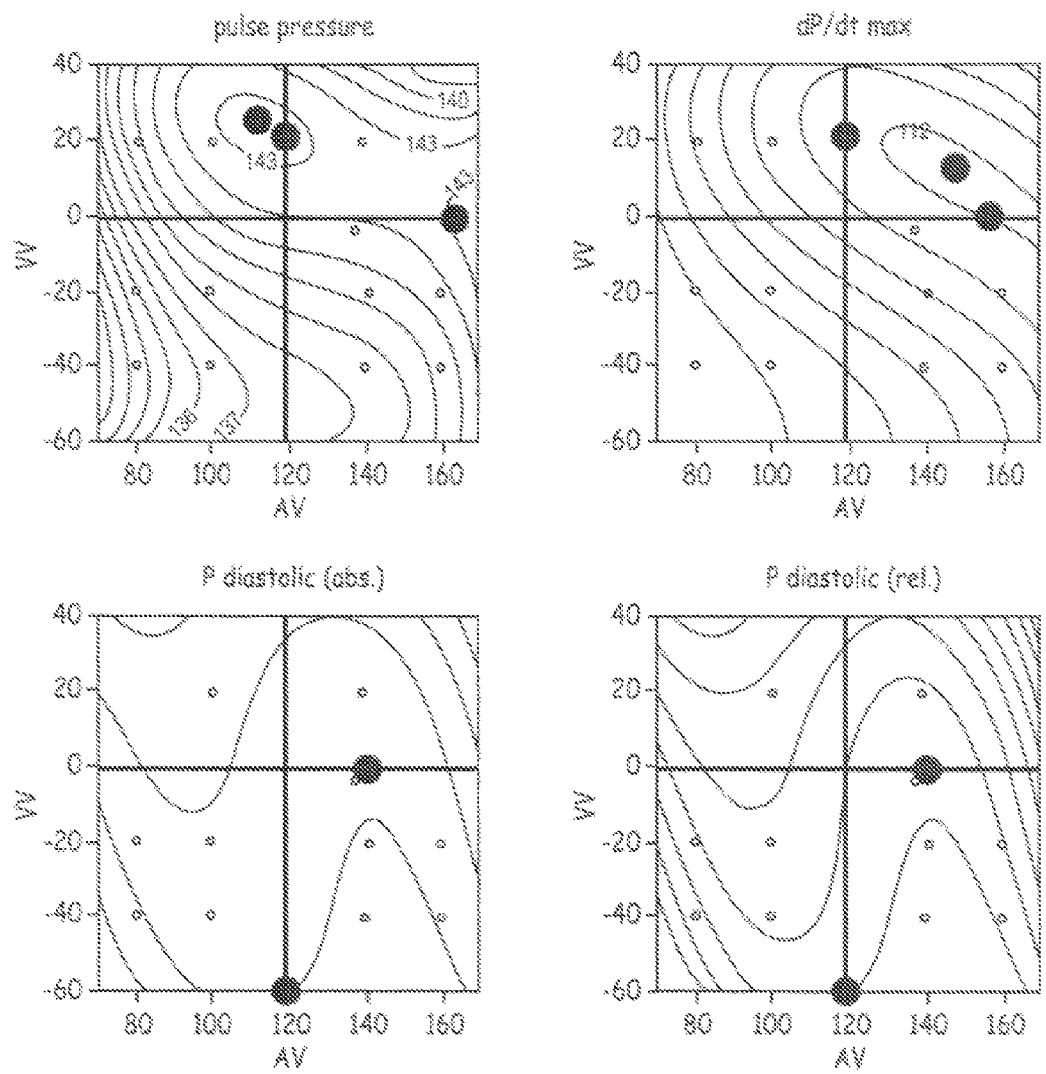
FIG. 5 is a graph demonstrating the dependence of left ventricular pulse pressure, dP/dt max, P diastolic (absolute) and P diastolic (relative) upon AV and VV intervals.

The superiority of concurrent pacing parameter optimization was demonstrated by an analysis of pacing parameter on 25 CRT patients. For each patient, three optimization routines were performed: AV only, VV only, and concurrent AV and VV. For AV only optimization, the AV interval was optimized by varying the AV interval through a set of values while the VV interval was held at the default value of zero. At each AV value, measures of cardiac function were made including LV pulse pressure, LV dP/dt max, LV absolute diastolic pressure and LV relative diastolic pressure. The results of the four measures of cardiac function are shown in FIG. 5. One or more of the resultant measures of cardiac function may be examined to determine the maximum cardiac function. For instance, dP/dt max may be used alone or in combination with the other resultant measures by known statistical analysis methods to identify the maximum cardiac function.

The optimal AV interval producing the maximum cardiac function was identified as approximately 132 ms. This optimization routine was repeated for VV only optimization, with the VV interval cycled through a set of values while the AV interval was held at a default value of 120 ms. The optimal VV interval was identified in the same manner as the optimal AV interval and was about −1.4 ms. Finally, the AV and VV intervals were optimized concurrently, which the AV and VV cycled through a set of combinations of intervals and cardiac function assessed as described for the AV only optimization. The optimal AV interval was identified as about 138 ms and the optimal VV interval was about −3.9 ms. Thus concurrent optimization identified a different optimal combination of pacing parameters than optimization of the AV and VV intervals individually.

Optimal pacing intervals may vary for an individual depending on the individual's state, such as physical state, activity level and hemodynamics. Therefore, in order to more precisely optimize pacing intervals, embodiments of this invention perform optimization of one or more pacing intervals in different states. Examples of states appropriate for distinct pacing parameter optimization routines include, for example, heart rhythm such as supraventricular tachycardia, pacing mode such as atrial sensed or atrially paced rhythm, heart rate and hemodynamic variables such as filling pressure, preload, afterload, systolic pressures, mean and minimum diastolic pressures, dP/dt, and pulse pressure. Other states for which optimization of pacing intervals may be appropriate include posture, intrinsic verses paced rhythm, presence or absence of a particular drug, $O_2$ saturation and degree of intracardiac dyssynchrony.

Optimization of pacing intervals for different states may be accomplished by segregating the states into different ranges or bins. For example, heart rate could be separated into different ranges such as 50-59, 60-69, 70-79 beats per minute, and so on. Similarly preload could be separated into ranges of ePAD such as less than 5 mmHg, 5-9 mmHg, 10-14 mmHg, 15-19 mmHg, 20-24 mmHg, and 25 or greater mmHg, for example. Smaller or larger ranges could be employed. Other states could be separated into two or more appropriate bins. For example, posture could be separated into bins such as prone and upright.

Optimization of one or more pacing intervals for different states may be performed individually, sequentially or concurrently as described above. Thus, for example, a first and a second pacing interval may be concurrently optimized by varying both intervals over a set of intervals and determining which combination of pacing intervals results in the maximum cardiac output for one range or bin for a particular state. This method of optimization could be repeated for each range or bin for that state. The result would be an optimum combination of first and second pacing intervals which would vary depending on the state. The IMD could be programmed to use the optimal set of pacing intervals for each corresponding range of a state. When a particular range of a state is detected, the IMD would provide the appropriate set of pacing intervals as determined by the optimization routine. When a new range of a state is detected, a different set of optimal pacing intervals would be applied.

Pacing interval optimization could be performed for a single state or for multiple states. When optimization is performed for multiple states, data regarding cardiac function could be gathered for each combination of pacing intervals at each combination of ranges or bins for each state. The resulting data can be used to create a multidimensional matrix of optimal combinations of pacing intervals which vary depending upon multiple states.

An optimization routine may be triggered in a variety of ways. The device may automatically begin an optimization routine periodically or in response to a trigger. For example, it may periodically cycle through an optimization routine with a predetermined frequency. Alternatively, the device may be triggered to initiate optimization by a physician or may be triggered by sensing particular information. For example, in some embodiments, optimization may be performed for states which are not controlled by the device, such as filling pressure, patient activity and posture. In these embodiments, the device may conduct optimization automatically when a state is detected as falling within a particular range of values. This type of trigger is particularly appropriate for ranges which occur infrequently.

Some states, such as hemodynamic states, are not directly controlled by the device. Examples of such states include right ventricular filling pressure, left ventricular filling pressure, activity and posture. In embodiments which optimize pacing parameters under varying conditions of such states, the device must wait to initiate each optimization routine until the appropriate range for the state is detected. Other states, such as heart rate, may be manipulated by the device. For example, the device may trigger a heart rate within a particular range and conduct a pacing parameter optimization routine while holding the heart rate in that range. The device may then trigger a heart rate in a different range and again conduct a pacing parameter optimization routine. The device could continue until it had performed such optimization for all desired heart rate ranges.

Alternatively, the device could wait until a heart rate within a range or bin is detected and conduct optimization at that time.

During optimization, the IMD device cycles through a set of pacing intervals. This set may include a range of physiologically acceptable pacing intervals. For example, the set of AV intervals applied during optimization may range from about 60 to about 250 ms. The interval may be evaluated at a variety of increments within this range, such as 5 ms or 10 ms, or a non-linear sampling scheme could be used. The set of VV intervals may range, for example, from about −100 to about +100 ms and may similarly be evaluated at increments such as 5 ms or 10 ms or a non-linear method of sampling could be used. The device may proceed systematically through the pacing interval values in the set or may select them randomly. In some embodiments, the device may first determine an approximate optimal set of intervals using intervals at greater increments such as 20 ms or 40 ms. It may then fine tune the optimal set of pacing intervals by applying more closely spaced pacing intervals, such as at 5 ms or 10 ms increments, in the proximity of the previously determined approximate optimum.

In addition to cycling through a physiologically acceptable set of pacing intervals, the device may also measure cardiac function using pacing intervals outside of a physiologically acceptable range. In this way, more data is obtained near the edge of the acceptable range of pacing intervals. This allows for improved mathematical extrapolation of the data by providing more data surrounding values at the edge of the range. Pacing intervals outside of the acceptable range which produce maximum cardiac function may not be considered optimal. Thus the IMD may exclude pacing intervals outside of the acceptable range from being identified as optimal pacing intervals.

The data regarding cardiac function at each combination of pacing intervals for a particular range of a state or states may be mathematically analyzed to identify the set of intervals which results in maximum cardiac function. For example, the data may be fitted using a using a $3^{rd}$ order polynomial. In this way, the combination of pacing intervals which produces the maximum cardiac function may be identified as the optimal combination of intervals for each range of one state or a combination of states. This analysis is repeated for each range of the state or states, until an optimal combination of intervals is identified for each range. The value of the optimal combination of intervals may be mathematically smoothed, such as by linear regression of the values, to avoid sharp transitions when an individual moves from one range of a state to an adjacent range of a state.

Once optimal pacing intervals are identified, the IMD may automatically reprogram itself to employ these intervals when the corresponding state is detected. Alternatively, a physician or other individual could verify the intervals prior to implementation by the IMD.

The invention claimed is:

1. A method of optimizing pacing intervals in an implantable cardiac stimulation device comprising:
    delivering biventricular stimulation at a first pacing interval and a second pacing interval;
    defining a range of hemodynamic values;
    detecting a hemodynamic state within the range of values;
    while the hemodynamic state remains within the range, concurrently cycling the first pacing interval and the second pacing interval through a set of combinations of differing ones of the values and measuring one or more cardiac function values to obtain cardiac function values for the set of combinations of values; and
    identifying the combination of first and second pacing intervals which produces a maximum cardiac function as being an optimal combination of intervals for the range of the hemodynamic state.

2. A method according to claim 1, further comprising programming the implantable cardiac stimulation device to provide cardiac stimulation at the identified optimal combination of first and second pacing interval values when the hemodynamic state is detected to be within the range.

3. A method according to claim 2, wherein the step of programming is performed automatically by the device.

4. A method according to claim 1, further comprising repeating the method of optimization for one or more additional ranges of values of the hemodynamic state to identify optimal combinations of pacing parameters for two or more ranges of the hemodynamic state.

5. A method according to claim 1, wherein the hemodynamic state comprises a preload pressure or a pulse pressure.

6. A medical device according to claim 1, wherein the implantable cardiac stimulation device comprises a cardiac resynchronization therapy device.

7. A method according to claim 1, wherein one of the first and second pacing intervals includes an AV interval.

8. A method according to claim 1, wherein one of the first and second pacing intervals includes a VV interval.

9. A method according to claim 1, wherein the set of values are predetermined.

10. A method according to claim 1, wherein values within the set of values are generated during optimization.

11. A method according to claim 1, wherein the pacing intervals are selected randomly from the set of values.

12. A method of optimizing pacing intervals in an implantable cardiac stimulation device comprising:
    delivering biventricular stimulation at a first pacing interval and a second pacing interval;
    defining a range of hemodynamic values;
    detecting a hemodynamic state within the range of values;
    while the hemodynamic state remains within the range, concurrently cycling the first pacing interval and the second pacing interval through a set of combinations of differing ones of the values and measuring one or more cardiac function values to obtain cardiac function values for the set of values; and
    identifying the combination of first and second pacing intervals which produces a maximum cardiac function as being an optimal combination of intervals for the range of the hemodynamic state; and
    wherein the first pacing interval and second pacing interval are cycled at each possible combination of first and second pacing intervals within the set of values.

13. A method according to claim 12, further comprising programming the implantable cardiac stimulation device to provide cardiac stimulation at the identified optimal combination of first and second pacing interval values when the hemodynamic state is detected to be within the range.

14. A method according to claim 13, wherein the step of programming is performed automatically by the device.

15. A method according to claim 12, further comprising repeating the method of optimization for one or more additional ranges of values of the hemodynamic state to identify optimal combinations of pacing parameters for two or more ranges of the hemodynamic state.

16. A method according to claim 12, wherein the hemodynamic state comprises a preload pressure or a pulse pressure.

17. A medical device according to claim 12, wherein the implantable cardiac stimulation device comprises a cardiac resynchronization therapy device.

18. A method according to claim 12, wherein one of the first and second pacing intervals includes an AV interval.

19. A method according to claim 12, wherein one of the first and second pacing intervals includes a VV interval.

20. A method according to claim 12, wherein the set of values are predetermined.

21. A method according to claim 12, wherein values within the set of values are generated during optimization.

22. A method according to claim 12, wherein the pacing intervals are selected randomly from the set of values.

* * * * *